United States Patent [19]

Baron

[11] 4,063,890
[45] Dec. 20, 1977

[54] METHOD AND APPARATUS FOR STERILIZING AND STORING CONTACT LENSES

[76] Inventor: Neville A. Baron, 8 Butterworth Drive, Morristown, N.J. 07960

[21] Appl. No.: 680,986

[22] Filed: Apr. 28, 1976

Related U.S. Application Data

[63] Continuation of Ser. No. 331,490, Feb. 12, 1973, abandoned.

[51] Int. Cl.² ............................................. A61L 13/00
[52] U.S. Cl. .............................. 21/54 R; 21/DIG. 2; 21/102 R
[58] Field of Search ............. 21/DIG. 2, 54 R, 102 R, 21/105; 206/5.1; 356/51

[56] References Cited

U.S. PATENT DOCUMENTS

| | | | |
|---|---|---|---|
| 2,235,296 | 3/1941 | Muncheryan | 21/102 R |
| 2,347,307 | 4/1944 | Whitman | 21/102 R |
| 2,537,530 | 1/1951 | Hofman | 21/102 R |
| 2,669,661 | 2/1954 | Riddiford et al. | 21/102 R |
| 3,268,068 | 8/1966 | Le Grand | 206/5.1 |
| 3,447,892 | 6/1969 | Watson et al. | 21/102 R |
| 3,504,683 | 4/1970 | Timmer et al. | 134/25 A |
| 3,519,005 | 7/1970 | Krezanoski et al. | 206/5.1 |
| 3,614,959 | 10/1971 | Schollmaier et al. | 206/5.1 |
| 3,683,177 | 8/1972 | Veloz | 21/102 R |
| 3,700,406 | 10/1972 | Landry | 21/102 R X |
| 3,700,761 | 10/1972 | O'Driscoll | 260/885 |
| 3,852,032 | 12/1974 | Urbach | 21/102 R |

OTHER PUBLICATIONS

Morton, "Introduction to Rubber Technology," Reinhold Publishing Corp., N.Y., pp. 134-135, 1959.
Luckiesh, "Applications of Germicidal Erythemal and Infrared Energy," D. Van Nostrand Co., N.Y., 1946, pp. 195-200.
Boucher, "Advances in Sterilization Techniques," Amer. J. Hospital Pharmacy, 29:660-672, Aug. 1972.

*Primary Examiner*—Barry S. Richman
*Assistant Examiner*—Arnold Turk

[57] ABSTRACT

A light-transmitting contact lens body of polymeric material is immersed in an aqueous liquid medium which is substantially transparent to the ultraviolet spectrum. The lens body and the liquid are irradiated with ultraviolet radiation sufficient to asepticize them but insufficient to cause significant molecular modification of the polymeric material.

6 Claims, 7 Drawing Figures

U.S. Patent Dec. 20, 1977 4,063,890
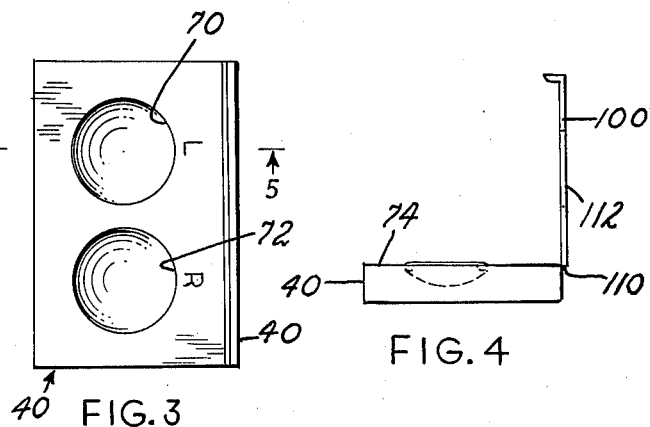
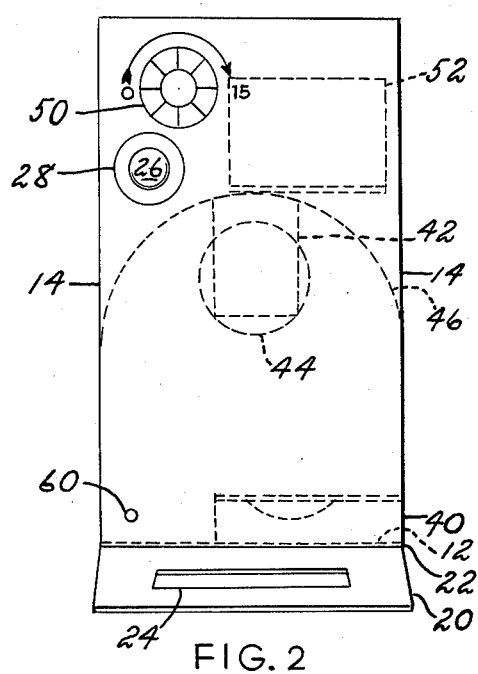
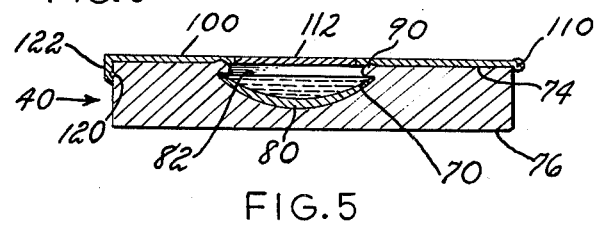
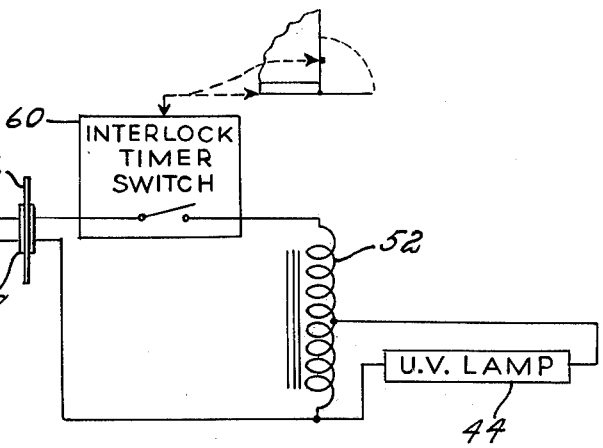
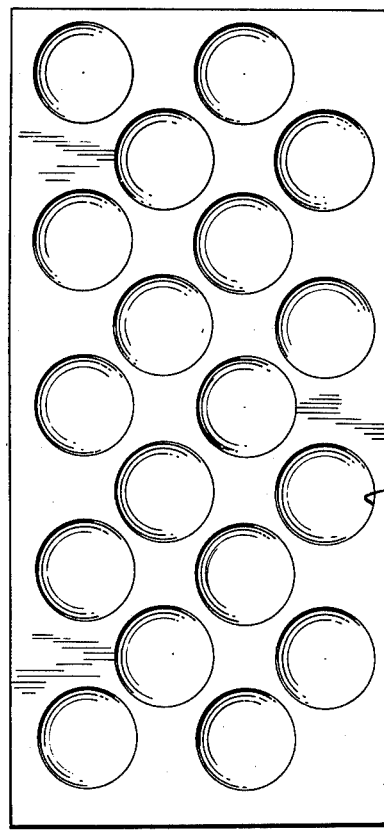
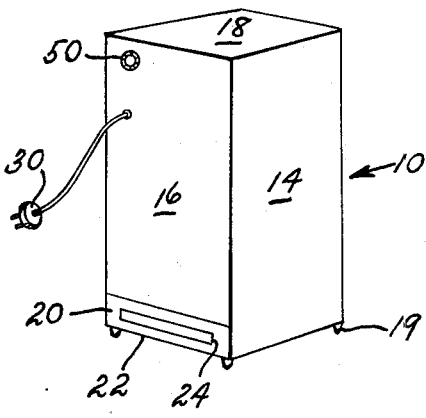

METHOD AND APPARATUS FOR STERILIZING AND STORING CONTACT LENSES

This application is a continuation of prior application Ser. No. 331490 filed Feb. 12, 1973, and now abandoned.

This invention relates to a process and apparatus for the asepticization of contact lenses. More particularly, it relates to a process and apparatus which are especially of value in asepticizing soft contact lenses.

It has previously been proposed to asepticize contact lenses by chemical treatments. This technique, while it may be of use in the asepticization of hard contact lenses, which typically are molded from polymethylmethacrylate, requires especially careful and thorough processing when considered with reference to soft contact lenses which characteristically are hydrophilic in nature and may contain a substantial (e.g., 35–65%) proportion of aqueous material in their structure.

It has also been proposed to asepticize soft contact lenses by boiling or exposure to steam. However, this is a cumbersome and time consuming process.

In accordance with the present invention, a process for asepticizing a light transmitting soft contact lens body of hydrophilia polymeric material comprises immersing said lens body in an aqueous liquid medium which is substantially transparent to radiation in the ultraviolet spectrum; and irradiating said lens body while in said aqueous liquid medium, and in the substantial absence of ozone, with ultraviolet radiation sufficient to asepticize said lens body and said aqueous liquid medium but insufficient to cause significant molecular modification of said hydrophilic polymeric material.

Also in accordance with the present invention is an apparatus for the asepticization of soft contact lenses which comprises a carrier member, said carrier member having therein at least two recesses each for accepting and holding a soft contact lens and sufficient liquid completely to envelop said lens, an asepticizing lamp, a covering over said lamp, said covering being opaque to asepticizing radiation from said lamp, and means for removably disposing said carrier member within said covering with said recesses in proximity to said lamp and exposed to asepticizing radiation therefrom.

The process and apparatus of the present invention make possible the extremely rapid and convenient asepticization of contact lenses with minimal crazing or degradation of the lens material and with no likelihood of introducing any undesirable foreign material into the eye when the lens is placed therein. In view of the ease and convenience with which asepticization is accomplished in accordance with the instant invention, the wearer of contact lenses is encouraged to observe faithfully a proper program of safe asepticization of his contact lenses.

The invention is illustrated in the accompanying drawings, in which:

FIG. 1 is a view in perspective of an apparatus constructed in accordance with the present invention;

FIG. 2 is a view in side elevation of one end of the apparatus of FIG. 1;

FIG. 3 is a plan view of a lens-carrying tray used in the apparatus of FIG. 1;

FIG. 4 is a view in side elevation of the tray of FIG. 3;

FIG. 5 is a view in cross-section on enlarged scale of the tray of FIG. 3 taken along the line 5—5 thereof;

FIG. 6 is a plan view of a lens-carrying tray similar to that of FIG. 3 but with a substantially greater number of lens-receiving wells, thus providing an apparatus for the use of the clinician who handles a substantial number of contact lenses simultaneously; and FIG. 7 is a partially schematic and partially pictorial diagram of the electrical circuit of the apparatus of FIG. 1.

Referring now more specifically to the drawings, a light-tight outer casing 10 of generally box-like configuration having a base 12, two side walls 14, two end walls 16, and a top 18, all of generally rectangular form, is fabricated of enameled steel so as to be light-impervious and resistant to mechanical shock. The base 12 of the casing 10 is aluminized on its inner surface, and affixed to its outer surface are four rubber feet 19. Across the bottom end of one end wall 16 is a door 20 affixed to the wall 16 by a spring hinge 22.

Mounted in an opening in the door 20 is a pilot light bezel 24 of translucent material carrying a phosphor. When illuminated with ultraviolet radiation, the phosphor-carrying bezel emits visible radiation without transmitting significant ultraviolet light through the casing 10.

A line cord 26 passes through a grommet 28 in one end wall 16 to supply electrical power to the apparatus. The line cord 26 terminates in a conventional male plug 30, permitting connection of the apparatus to 120/230 volt a.c. mains.

As can be seen in FIG. 2 in which the door 20 is illustrated in its open position, a tray 40 is housed resting on the base 12 of the outer casing 10 behind the normally closed door. Also illustrated in FIG. 2 is a lampholder 42 which positions a cylindrical ultraviolet lamp 44 about two inches from the tray, near the focal point of a polished aluminum reflector 46 which directs radiation from the lamp 44 towards the tray 40. Additionally, a calibrated timer control 50 projects outwardly from one end wall 16, a voltage-reducing autotransformer 52 is housed in the upper part of the casing, above the reflector 46, and a normally open actuating switch 60, which also acts as an interlock, is positioned near the bottom of the casing 10 behind the normally closed door 20. The normally open switch 60 is controlled by a mechanical linkage which permits the door 20 to close it to the "on" position only when the tray 40 is fully inserted. Any time the door 20 is opened, or the tray 40 is not in place, the switch 60 remains open.

The tray 40 is best illustrated in FIGS. 3–5.

The tray 40 constitutes a horizontal slab-like body having a pair of wells 70 and 72 recessed into the upper surface 74 of the body. The slab-like body is molded of Lexan, (4,4 isoprophlidenediphenol polymerized to a molecular weight of about 30,000–35,000) a transparent polycarbonate resin. The lower surface 76 of the slab is mirrored to form a reflecting surface.

The wells 70 and 72 are individually identified by letters ("L" and "R") integral with the slab, to permit the user to distinguish the eyes for which the contact lenses 80 placed therein are prescribed.

The recessed wells 70 and 72 are generally of spherical contour, and are of volume sufficient each to accept and retain a contact lens and sufficient liquid (sterile isotonic saline solution) 82, i.e., about 1 ml. thereof, completely to cover the lens. Thus, the wells 70 and 72 have a maximum diameter of about 17 mm. and a volume of about two cubic centimeters.

At the top of each well 70 and 72 a small lip 90 is molded into the tray 40. The lip 90 projects inwardly over the well opening and facilitates disposition of the lens 80 in the well. The lip 90 also projects upwardly to provide a liquid- and air-tight seal against a rigid cover 100 of polymethylmethacrylate.

The cover 100 is hard and rigid relative to the tray and is affixed to the relatively softer and more resilient polycarbonate tray by a hinge 110.

In order to ensure maximum transmission of ultraviolet energy from the lamp 44 into each lens 80, the cover 100 is provided with an ultraviolet-transparent quartz window 112. This window extends entirely over the opening of each well 70 and 72. Each quartz window is circular, having a diameter of approximately 17 mm. and a thickness of about 3 mm.

A projection 120 on a side wall of the tray 40 frictionally engages a recess in a downwardly projecting lip 122 on the cover to retain it in closed position for storage of lenses and lens-covering saline solution both before and after asepticization.

The alternative tray construction shown in FIG. 6 is suitable for use when it is desired to asepticize more than a pair of lenses at a time. In this embodiment, a polycarbonate tray 140 is provided with a series of staggered pairs of wells 170 which are laterally sequentially offset from the longitudinal centerline of the tray. This disposition of wells 170 facilitates relatively uniform exposure of the retained lenses to ultraviolet radiation. (Preferably the tray 140 is inserted in the casing 10 with the longitudinal centerline of the tray directly below the longitudinal axis of the cylindrical tubular lamp 44.)

The electrical circuit employed in the instant apparatus is best illustrated in FIG. 7. As illustrated, the ultraviolet lamp 44 is supplied with power from the voltage-reducing transformer 52. However, if desired, a voltage-dropping resistor may be employed in place of the transformer. The operation of the interlock switch 60 has been described previously. The duration of the time cycle during which the timer switch supplies power to the lamp is controlled by a mechanical escapement set by the user by means of the control knob 50. The escapement is set to provide irradiation for a period having a minimum duration in excess of that required for complete asepticization under the conditions and characteristics of the lamp and lamp-to-tray distance utilized in the apparatus. Thus, an exposure of at least 5 and up to a maximum of 20 seconds to radiation from a 4 watt G475 lamp at a lens-to-lamp distance of about two inches is contemplated.

In use, a user of contact lenses formed of about 61% loosely cross linked poly(2-hydroxyethylmethacrylate) and 39% water, (or comparable transparent hydrophilic lenses such as those containing about 60% by weight of water) prepares a well 70 by depositing about 1 ml. of sterile saline solution (0.9% sodium chloride) 82 therein. A lens 80 is then removed from an eye where it is hydrated and softened by the tear film (or other location) and placed in a well with the saline solution, which is present in amount sufficient to cover the lens. (The lens is, of course, placed in the appropriate well, "L" 70 or "R" 72, depending on the eye for which it has been prescribed.)

After the lens has been placed in the appropriate well and is immersed in saline solution, the lens in the user's other eye is similarly removed and completely immersed in saline in the well provided therefor.

Thereafter, the cover 100 is secured over the wells 70 and 72, closing them in an air-and liquid-tight manner. The male plug 30 is connected to the a.c. mains, and the timer control 50 is set for the desired exposure. The user then opens the door 20 against the pressure of the spring hinge 22 and inserts the tray 40 into the base of the casing 10 in the opening provided.

After the tray and its contents are fully inserted into the casing, the door 20 is released and is closed by the action of the spring hinge 22. The conjoint action of the tray 40 and the inner surface of the door 20 on the interlock switch 60 closes the switch, providing power which lights the the lamp 44 for the period of time determined by the switch 60.

As indicated above, this time period is sufficient to effect complete asepticization of the lenses and solution contained in the tray but is not excessive and does not incur material molecular modification of the polymeric lens structure.

During the period of irradiation, the bezel 24 glows and indicates that irradiation is occurring.

The ultraviolet irradiation employed in the process and apparatus of the instant invention is of a wavelength longer than 221 nanometers, and preferably longer than 240 nanometers, thereby accomplishing asepticization in the substantially complete absence of ozone. The duration of the asepticizing exposure is controlled to be greater than the minimum necessary for complete asepticization of the lenses being treated but insufficient to shorten unnecessarily the half-life of the polymeric lens or the useful life of the ultraviolet lamp.

After the lenses and enveloping saline have been asepticized, they are stored in the covered, sealed tray until needed for use. The tray may be left in the casing 10, or removed and stored elsewhere, i.e., carried with the user, as desired. When desired for use, the cover 100 is removed from the tray 40, and the appropriate lens 80 is removed from the well and the liquid in which it is stored and is inserted in the eye in the customary manner.

It is to be understood that the invention herein illustrated and described is to be limited only by the scope of the claims appended hereto, and that various changes, modifications and equivlents may be substituted without departing from the true spirit of the invention. Thus, for example, in lieu of saline solution, distilled water or other suitable aqueous solution may be employed, and a rechargeable battery or other source may be employed as a source of electric power.

What is claimed is:

1. A process for asepticizing a light transmitting soft contact lens body of hydrophilic polymeric material which comprises hydrating said lens body with an aqueous liquid medium which is substantilly transparent to radiation in the ultraviolet spectrum; and irradiating said lens body for a timed period of discrete duration while hydrated with said aqueous liquid medium, with ultraviolet radiation of a wavelength sufficient to asepticize said lens body and said aqueous liquid medium in the substantial absence of ozone but insufficient to cause significant molecular modification of said hydrophilic polymeric material.

2. A process for asepticizing a light transmitting soft contact lens body of hydrophilic polymeric material which comprises disposing said soft contact lens on a liquid-retaining carrier; immersing said lens body while on said carrier in an aqueous liquid medium which is substantially transparent to radiation in the ultraviolet spectrum; irradiating said immersed lens body for a timed period of limited, discrete duration with ultraviolet radiation of a wavelenght sufficient to asepticize said lens body and said aqueous liquid medium in the substantial absence of ozone but insufficient to cause significant molecular modification of said hydrophilic polymeric material; and thereafter storing said asepticized lens body in said asepticized aqueous liquid medium.

3. A process for the asepticization and storage of a soft contact lens which comprises disposing a light transmitting, non-sterile soft contact lens body of hydrophilic polymeric material in a liquid retaining carrier, said carrier being at least in part substantially transparent to radiation in the ultraviolet spectrum, immersing said lens body while in said carrier in a sterile aqueous liquid medium which is substantially transparent to radiation in the ultraviolet spectrum, disposing said lens body while in said aqueous liquid medium in proximity to a source of ultraviolet radiation, irradiating said lens body through said aqueous liquid medium and in the substantial absence of ozone with ultraviolet energy from said source thereof and exposing, for a timed exposure of up to twenty seconds, said lens to energy in the ultraviolet spectrum of a wavelength sufficient to asepticize said entire lens body and aqueous liquid medium in the substantial absence of ozone, terminating said irradiation after said lens body and aqueous medium are asepticized and before the occurrence of significant molecular modification of said hydrophilic polymeric material, and thereafter storing said asepticized lens body in said asepticized aqueous liquid medium.

4. An apparatus for the asepticization of soft contact lenses in the substantial absence of ozone which comprises a carrier member, said carrier member having therein at least two recesses each for accepting and holding a soft contact lens and sufficient liquid completely to envelop said lens, an ultraviolet asepticizing lamp for generating asepticizing radiation in the substantial absence of ozone, a covering over said lamp, said covering being opaque to asepticizing radiation from said lamp, means for removably disposing said carrier member within said covering with said recesses in proximity to said lamp and exposed to asepticizing radiation having a wavelength longer than 221 nanometers therefrom, and a timer for regulating the period of exposure to said radiation of said lens while in said carrier.

5. Apparatus of asepticizing soft contact lenses in the substantial absence of ozone which comprises a carrier member, said carrier member having a base and a cover, said base having thereon at least two recesses, each recess being adapted to accept and hold a soft contact lens together with sufficient liquid completely to envelop said lens; said cover being transparent to ultraviolet radiation; a source of asepticizing ultraviolet radiation having a wavelength longer than 221 nanometers; a timer for controlling the period of duration of asepticizing radiation; means for enclosing said radiation source, said enclosing means being opaque to said asepticizing radiation; and means for accepting said carrier member within said enclosing means with said recesses in the base of said carrier means being positioned to receive said timed asepticizing radiation from said source thereof.

6. Apparatus as set forth in claim 5 in which said cover removably seals at least one of said recesses in a liquid tight manner.

* * * * *